US009665639B2

(12) United States Patent
Mashin-Chi et al.

(10) Patent No.: US 9,665,639 B2
(45) Date of Patent: May 30, 2017

(54) DETECTING FECAL AND URINE EVENTS BY REFERENCE TO COLLECTIONS OF DATA

(71) Applicant: Fred Bergman Healthcare PTY LTD, North Sydney (AU)

(72) Inventors: Hadi Mashin-Chi, North Bondi (AU); David Albert Barda, Rose Bay (AU); Jian Huang, North Sydney (AU)

(73) Assignee: Fred Bergman Healthcare Pty. Ltd., North Sydney (AU)

( * ) Notice: Subject to any disclaimer, the term of this patent is extended or adjusted under 35 U.S.C. 154(b) by 0 days.

(21) Appl. No.: 14/951,797

(22) Filed: Nov. 25, 2015

(65) Prior Publication Data

US 2016/0147865 A1    May 26, 2016

Related U.S. Application Data

(63) Continuation-in-part of application No. 14/130,833, filed as application No. PCT/AU2012/000806 on Jul. 5, 2012.

(60) Provisional application No. 61/544,340, filed on Oct. 7, 2011, provisional application No. 61/505,082, filed on Jul. 6, 2011.

(51) Int. Cl.
*G06F 17/30*    (2006.01)
*G06F 19/00*    (2011.01)

(52) U.S. Cl.
CPC ...... *G06F 17/30598* (2013.01); *G06F 19/345* (2013.01)

(58) Field of Classification Search
None
See application file for complete search history.

(56) References Cited

U.S. PATENT DOCUMENTS

| 4,846,190 A | * | 7/1989 | John | A61B 5/04021 600/544 |
| 2004/0220538 A1 | * | 11/2004 | Panopoulos | A61F 13/42 604/361 |
| 2004/0243328 A1 | * | 12/2004 | Rapp | A61B 5/4094 702/71 |

* cited by examiner

*Primary Examiner* — Syed Hasan
(74) *Attorney, Agent, or Firm* — Hansen IP Law PLLC

(57) ABSTRACT

A method for analyzing incoming data, comprising the steps of processing the incoming data in segments to output a sequence of segment types by extracting one or more properties of an incoming data segment and forming an Unknown Property Vector for each segment of data in the incoming data, and processing the sequence of segment types to identify events in the incoming data. The sequence of segment types is determined, for each segment, by analyzing the Unknown Property Vector by reference to one or more collections of vectors obtained from a set of Reference Property Vectors. This may each of the one or more collections of vectors being selected from the set of Reference Property Vectors randomly or based on relevance or clustering.

7 Claims, 7 Drawing Sheets

| Event Sequence Identifier | Peak value of the previous event | Length from the previous peak | Windows properties | Segment's type |
|---|---|---|---|---|
| 1 | x | x | x | 1 |
| 1 | x | x | x | 2 |
| 2 | x | x | x | 1 |
| 2 | x | x | x | 1 |
| 2 | x | x | x | 2 |
| 2 | x | x | x | 1 |
| 3 | x | x | x | 2 |
| 4 | x | x | x | 1 |
| 4 | x | x | x | 0 |

| Event Sequence Identifier | Peak value of the previous event | Length from the previous peak | Windows properties | Segment type |
|---|---|---|---|---|
| 2 | x | x | x | 1 |
| 2 | x | x | x | 1 |
| 2 | x | x | x | 2 |
| 2 | x | x | x | 1 |

Fig. 9

| Event Sequence Identifier | Peak value of the previous event | Length from the previous peak | Windows properties | Segment type | Euclidian distance |
|---|---|---|---|---|---|
| 2 | x | x | x | 1 | 1.7 |
| 2 | x | x | x | 1 | 1.8 |
| 2 | x | x | x | 2 | 1.3 |
| 2 | x | x | x | 1 | 1.1 |

Fig. 10

| Event Sequence Identifier | Peak value of the previous event | Length from the previous peak | Windows properties | Segment type | Euclidian distance |
|---|---|---|---|---|---|
| 2 | x | x | x | 1 | 1.1 |
| 2 | x | x | x | 2 | 1.3 |
| 2 | x | x | x | 1 | 1.7 |
| 2 | x | x | x | 1 | 1.8 |

Fig. 11

| Event Sequence Identifier | Peak value of the previous event | Length from the previous peak | Windows properties | Segment type | Euclidian distance |
|---|---|---|---|---|---|
| 2 | x | x | x | 1 | 1.1 |
| 2 | x | x | x | 1 | 1.2 |
| 2 | x | x | x | 2 | 1.3 |

Fig. 12

DETECTING FECAL AND URINE EVENTS BY REFERENCE TO COLLECTIONS OF DATA

CROSS REFERENCE TO RELATED APPLICATIONS

This application is a continuation-in-part of U.S. patent application Ser. No. 14/130,833, filed Apr. 29, 2014, which is a 35 U.S.C. §371 national phase entry of Patent Cooperation Treaty Application No. PCT/AU2012/000806, filed Jul. 5, 2012, which claims the benefit of U.S. Provisional Patent Application Nos. 61/544,340, filed Oct. 7, 2011, and 61/505,082, filed Jul. 6, 2011. The entirety of each of the foregoing applications is hereby incorporated by reference.

FIELD OF THE INVENTION

This invention relates to methods, systems, computer program products, devices and related aspects for improving event detection using signals obtained from sensors. The invention relates particularly but not exclusively to processing of sensor signals obtained from wetness sensors such as those that may be employed to detect urine and faecal events in incontinence pads, diapers, nappies, wound dressings and the like.

BACKGROUND TO THE INVENTION

Incontinence is a condition in which there is an uncontrolled release of discharges or evacuations. Urinary incontinence refers to loss of bladder control resulting in involuntary or uncontrolled urination. Other forms of incontinence include faecal or bowel incontinence.

Treatment options for incontinence can include behaviour management, medication and surgery. In circumstances where treatment is not available or unsuccessful, the only option is to address the incontinence events themselves. Such methods include the incontinent individual wearing an absorbent pad, diaper or nappy.

Most incontinent individuals are elderly or suffer from some form of disability or cognitive impairment. Accordingly, a significant proportion of incontinent individuals reside in care institutions such as nursing homes, aged care facilities and geriatric institutions as well as hospitals. Many of these individuals suffer from incontinence events on a regular basis. Additionally, infants and toddlers are incontinent individuals who, although they typically do not reside in care institutions, may benefit from the present invention.

To comply with care regulations and protocols it is necessary for staff to conduct manual checks of incontinent individuals on a regular basis. These manual checks are typically carried out irrespective of whether the individual has actually suffered an incontinence event. Often, the individual is unwilling or unable to cooperate and/or alert staff of the fact that an incontinence event has occurred. As can be appreciated, the need to conduct regular checks of individuals for the occurrence of an incontinence event places a significant burden on the resources of care institutions and also causes interruption to the individual's day to day activities, including their rest and sleep.

Incontinence indicators and detection systems exist. However, generally these are unable to distinguish e.g. a urinary incontinence event from a faecal incontinence event. Furthermore, existing incontinence detection systems are typically unable to detect or provide useful information about individual events such as the volume of a particular event.

Most often, existing incontinence detection systems merely alert carers to the occurrence of an event so that the carer may then attend to changing of the pad or diaper. However, often times the incontinence event may not be significant enough to warrant changing of the diaper. Accordingly, the alerting system may lead to loss of time and/or resources.

Attempts to refine existing systems or to develop new systems which provide improved and/or enhanced wetness event detection have been frustrated by difficulties in sensor signal processing, producing erroneous and often useless results. As a result, such systems have failed once deployed in actual care scenarios and carers revert to the traditional methods of manual checking. The present invention seeks to ameliorate or improve upon signal processing that may be used to provide improved wetness detection systems, particularly as may be applied in monitoring individuals who experience the condition of incontinence.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge as at the priority date of any of the claims.

SUMMARY OF THE INVENTION

Accordingly, in one aspect, the present invention provides a method for analysing incoming data, comprising the steps of:

(a) processing the incoming data in segments to output a sequence of segment types by extracting one or more properties of an incoming data segment and forming an Unknown Property Vector for each segment of data in the incoming data; and (b) processing the sequence of segment types to identify events in the incoming data;

wherein the sequence of segment types is determined, for each segment, by analysing the Unknown Property Vector by reference to one or more collections of vectors from a set of Reference Property Vectors.

The incoming data may be data from any source. In a preferred embodiment, the incoming data is sensor data from a wetness sensor, and the events identified are wetness events and/or faecal events. It is to be understood, however that wetness-related events such as odour events or audible events may be identified in addition to or as an alternative to detection of wetness per se, employing the methods, systems and other aspects of the present invention.

In an embodiment, each of the one or more collections of vectors includes vectors randomly selected from the set of Reference Property Vectors. Accordingly, in such embodiments, the number of Reference Property Vectors used in analysing the Unknown Property Vector is reduced to a smaller number. The number of Reference Property Vectors may be reduced randomly, e.g., a random subset of the Reference Property Vector is chosen. Processing of the incoming data can be achieved more quickly if the number of Reference Property Vectors is reduced which is particularly advantageous if the data needs to be processed as fast as possible.

In embodiments, each of the one or more collections of vectors are:
a) derived from the set of Reference Property Vectors; or
b) chosen from the set of Reference Property Vectors to form a subcollection of the set of Reference Property Vectors; or
c) both a) and b).

Accordingly, embodiments of the invention call for the Reference Property Vectors to be divided or split into one or more collections or subsets and for the processing to be performed on each of the collections or subsets. The results can then be aggregated to determine the segment type. The dividing or splitting of the Reference Property Vectors into collections is advantageous when dealing with large data sets in such a way that computational analysis can be performed in a timely, computationally efficient and cost effective manner. On the other hand, reducing the number of Reference Property Vectors for the purposes of computational analysis by dividing or splitting of the Reference Property Vectors into collections may impact the accuracy of the analysis. To improve the accuracy of the analysis more sophisticated approaches than randomly reducing the Reference Property Vector are envisaged.

Preferably, each of the one or more collections of vectors are determined by reference to the Unknown Property Vector.

In embodiments, each of the one or more collections of vectors includes vectors randomly selected from the set of Reference Property Vectors.

In embodiments, each of the one or more collections of vectors includes one or more vectors representative of groups or clusters of vectors from the set of Reference Property Vectors.

Accordingly, embodiments of the invention can include a process of selecting a set of candidates wherein each candidate represents a group or cluster of the Reference Property Vectors. The group or cluster of the Reference Property Vectors may be grouped or selected based on their similarity. One way of grouping or selecting similar Reference Property Vectors is to perform a clustering analysis in which each of the Reference Property Vectors which have a similar property are grouped in a cluster. Each cluster can then be represented by one or more candidates (which may also be described as representative vectors). For example the centre of the cluster can represent the cluster or the centre of the more populated space in the cluster may be the candidate (representative vector) of the cluster. Similarly more than one candidate (representative vector) can represent a cluster. In any of the embodiments involving a candidate or representative vector a set of Reference Property Vectors of lib-size vectors is reduced to cluster-num*candidate-per-cluster candidates in which cluster-num is the number of clusters and candidate-per-cluster is the number of candidates chosen to represent each cluster. The segment type of each candidate of each cluster is the representation of all the Reference Property Vectors segment types in that particular cluster. For example the segment type of a candidate of a cluster can be an average of all the segment types of the Reference Property Vectors in that cluster. In another example the segment type of a candidate of a cluster can be a weighted average in which the segment types of the Reference Property Vectors, in the cluster which are more similar (or are closer if a distance measurement is chosen) to the candidate, have more impact on the segment type of the candidate.

Preferably, the one or more collections of vectors are distributed across one or more storage devices.

In embodiments, the sequence of segment types is determined, for each segment, by comparing the Unknown Property Vector with the one or more collections of vectors in parallel.

In embodiments, the Unknown Property Vector is compared with the one or more collections by more than one processing device operating in parallel.

Preferably, the sequence of segment types is determined, for each segment, by aggregating results of the analysis of the Unknown Property Vector by reference to the one or more collections of vectors.

Preferably, the sequence of segment types is determined, for each segment, by reference to a subcollection of vectors of each one or more collections of vectors that are relevant to the Unknown Property Vector.

The subcollection of vectors can be a selection of vectors from each of the one or more collections of vectors in respect of which at least one of the properties is relevant to the same property of the Unknown Property Vector.

The subcollection of vectors can include vectors in respect of which at least one of the properties are relevant, more relevant, similar or more similar to the same property of the Unknown Property Vector.

The subcollection of vectors can exclude vectors in respect of which at least one of the properties are least relevant or are dissimilar to the same property of the Unknown Property Vector.

In some embodiments, during the processing of the incoming data in segments the Reference Property Vectors which are relevant (or more relevant) or similar (or more similar) to the Unknown Property Vector are included in the collection(s), set(s) or sub-set(s), or alternatively the Reference Property Vectors which are not relevant (or less relevant), not similar (less similar) or dissimilar (more dissimilar) to the Unknown Property Vector are removed. The relevant subset is identified based on the similarity of at least a property in an Unknown Property Vector to the same or an associated property in the Reference Property Vectors. For example if the $3^{rd}$ and the $5^{th}$ properties are used for determining similar vectors (or alternatively removing dissimilar vectors), then when an Unknown Property Vector is analysed, the Reference Property Vectors with similar values for the $3^{rd}$ and $5^{th}$ properties to the values for the $3^{rd}$ and $5^{th}$ properties of the Unknown Reference Property Vector are included in the collection(s), set(s) or sub-set(s), (or the dissimilar ones are removed).

In embodiments, the subcollection of vectors is determined by a hierarchical procedure of including vectors that comprise two or more of the properties that are relevant or similar in a hierarchical order to the same two or more of the properties of the Unknown Property Vector.

In embodiments, the subcollection of vectors is determined by a parallel procedure of including vectors that comprise two or more of the properties that are relevant or similar in no particular order to the same two or more of the properties of the Unknown Property Vector.

The similarity can be measured by a similarity measurement such as measuring the similarity of values of one or more properties in a vector to associated values of one of more properties of another vector, e.g., Euclidean distance of two vectors or Euclidean distance of a value of at least one property of two vectors. The properties that are used for removing vectors include the following non-limiting examples, namely: sequence ID, pad type, pad size, gender, or other properties. In another embodiment, a weight may be applied to each of the used properties, e.g. weighted distance.

Accordingly, in some embodiments, the subcollection of vectors is determined from the set of Reference Property Vectors in a hierarchical procedure of including in the set of the subcollection of vectors the Reference Property Vectors that comprise two or more of the properties that are relevant, more relevant, similar or more similar in a hierarchical order to the same two or more of the properties of the Unknown Property Vector.

In the hierarchical procedure, at least one of the properties is used to remove the vectors that are not similar to the Unknown Property Vector and then the same procedure may apply with a different one or more properties of the remaining vectors. In other embodiments, determining the subcollection of vectors includes a parallel procedure of including in the set of the selected vectors the Reference Property Vectors that comprise two or more of the properties that are relevant, more relevant, similar or more similar in no particular order to the same two or more properties of the Unknown Property Vector. Accordingly, in the parallel procedure, at least a property is used to remove the vectors that are not similar to the Unknown Property Vector.

Preferably, the subcollection of vectors is a selection of vectors from each of the one or more collections of vectors in respect of which at least one of the properties is a distance apart from the same one or more properties of the Unknown Property Vector that is less than a threshold.

In embodiments, the threshold is static or dynamic.

The dynamic threshold may change depending and/or based on one or more of the following:
  number of detected wetness events;
  segment types of previous segments;
  geographical origin of incoming data; and
  physiological information of a person from whom the incoming data originates.

Preferably, the properties of the incoming data segment are derived from an intersection of the incoming data with the one or more boundaries of a moving window.

The properties of the incoming data segment can be derived from a plurality of intersections of the incoming data with the one or more boundaries of the moving window.

In another aspect, the present invention provides a wetness event detection system for processing sensor signals to detect wetness events in sensor data obtained from one or more wetness sensors in a pad worn by a subject, the system including:
(a) an input module configured to receive and optionally pre-process sensor signals from the one or more wetness sensors;
(b) a storage module configured to store reference wetness data;
(c) processing means configured to process sensor data from the input module to identify wetness events in the sensor data;
(d) a memory module storing instructions that are executable to cause the processor to perform a method of analysing sensor data;
(e) a user interface configured to receive inputs from a user; and
(f) a display means communicatively coupled with the processing means and configured to display wetness event information derived from the processing means,
wherein the processing means processes the sensor data to output a sequence of segment types by extracting one or more properties of an incoming data segment and forming an Unknown Property Vector for each segment of data in the incoming data; and processing the sequence of segment types to identify events in the incoming data; wherein the sequence of segment types is determined, for each segment, by analysing the Unknown Property Vector by reference to one or more collections of vectors from a set of Reference Property Vectors.

The memory module preferably stores instructions that are executable to cause the processor to perform a method of analysing data according to the first aspect of the invention and embodiments thereof described above.

In another aspect, the invention provides a computer program product storing executable instructions readable by a processing means and causing the processing means to process incoming data, the instructions causing the processing means to perform steps including:
(a) processing the incoming data in segments to output a sequence of segment types by extracting one or more properties of the incoming data segment to form an Unknown Property Vector for each segment of data in the incoming data; and
(b) processing the sequence of segment types to identify events in the incoming data, wherein the sequence of segment types is determined, for each segment, by analysing the Unknown Property Vector by reference to one or more collections of vectors from a set of Reference Property Vectors.

Preferably, the processing means is operable to perform a method of analysing data according to the first aspect of the invention and embodiments thereof described above.

In yet another aspect, the present invention provides a transmission device for transmitting data to a server indicative of signals received from a wetness sensor in an absorbent article, the device being operable for:
receiving signals from a wetness sensor in an absorbent article;
transmitting data indicative of the signals received from the wetness sensor to a server operable for:
  (a) processing the incoming data in segments to output a sequence of segment types by extracting one or more properties of the incoming data segment to form an Unknown Property Vector for each segment of data in the incoming data; and
  (b) processing the sequence of segment types to identify urinary or faecal events in the incoming data, wherein the sequence of segment types is determined, for each segment, by analysing the Unknown Property Vector by reference to one or more collections of vectors from a set of Reference Property Vectors; and
receiving information from the server indicative of the occurrence of a urinary or faecal event in the absorbent article.

The device preferably includes an alert means for issuing an alert of the occurrence of a urinary or faecal event in the absorbent article.

Preferably, the server is operable for performing the method of analysing data according to the first aspect of the invention and embodiments thereof described above.

The transmission device can include an alert means for issuing an alert of the occurrence of a urinary and/or faecal event in the absorbent article, said alert means in the form of:
a) a vibrating device; or
b) a device for generating a sound; or
c) a flashing light; or
d) any combination of a), b) and c).

In another aspect, the present invention provides a presentation device for presenting the occurrence of a urinary and/or faecal event in an absorbent article, the device being operable for receiving a signal representing the occurrence of a urinary and/or faecal event in an absorbent article from a server, the server operable for:
(a) processing a sensor data from the absorbent article in segments to output a sequence of segment types by extracting one or more properties of the sensor data segment to form an Unknown Property Vector for each segment of data in the sensor data; and (b) processing the sequence of segment types to identify urinary and/or faecal events in the sensor data, wherein the sequence of segment types is determined, for each segment, by analysing the Unknown Property Vector by reference to one or more collections of vectors from a set of Reference Property Vectors; and receiving information from the server indicative of the occurrence of a urinary or faecal event in the absorbent article and presenting the occurrence of the event.

The presentation device can include an alert means for issuing an alert of the occurrence of a urinary and/or faecal event in the absorbent article, the alert means being operable for:

a) vibrating the device; or
b) generating a sound; or
c) flashing light; or
d) any combination of a), b) and c).

In embodiments, the presentation device receives information from a server operable to perform a method of analysing incoming data in accordance with an aspect of the invention, and embodiments thereof, as described above.

Throughout this specification, various processing steps are described and in some examples and embodiments discussed, the data and segments of data are referred to as being processed in sequence. It is to be understood, however, that the invention, in its broader application is not limited to sequential processing of data segments, or of windows of data, and that in many steps non-sequential data processing is contemplated though not always explicitly stated.

BRIEF DESCRIPTION OF THE DRAWINGS

The present invention will now be described in greater detail with reference to the accompanying drawings. It is to be understood that the embodiments shown are examples only and are not to be taken as limiting the scope of the invention as discussed herein and defined in the provisional claims appended hereto.

FIG. 7 is a schematic illustration of a wetness event detection system according to an embodiment of the present invention.

FIGS. 8 to 12 contain entries representing sets of Reference Property Vectors (RPV) that are progressively reduced in size during a process of determining a segment type for a segment of data represented in an Unknown Property Vector (UPV), according to an embodiment of the invention.

DETAILED DESCRIPTION OF THE INVENTION

According to an embodiment of the invention, a method for processing a stream of incoming data, particularly data from one or more wetness sensors, requires comparing property vectors obtained from the incoming data with a set of Reference Property Vectors obtained from historical or reference data.

The method broadly includes processing the incoming data in segments to output a sequence of segment types by extracting one or more properties of an incoming data segment and forming an Unknown Property Vector for each segment of data in the incoming data; and processing the sequence of segment types to identify events in the incoming data, wherein the sequence of segment types is determined, for each segment, by analysing the Unknown Property Vector by reference to one or more collections of vectors from a set of Reference Property Vectors.

Figure 1:
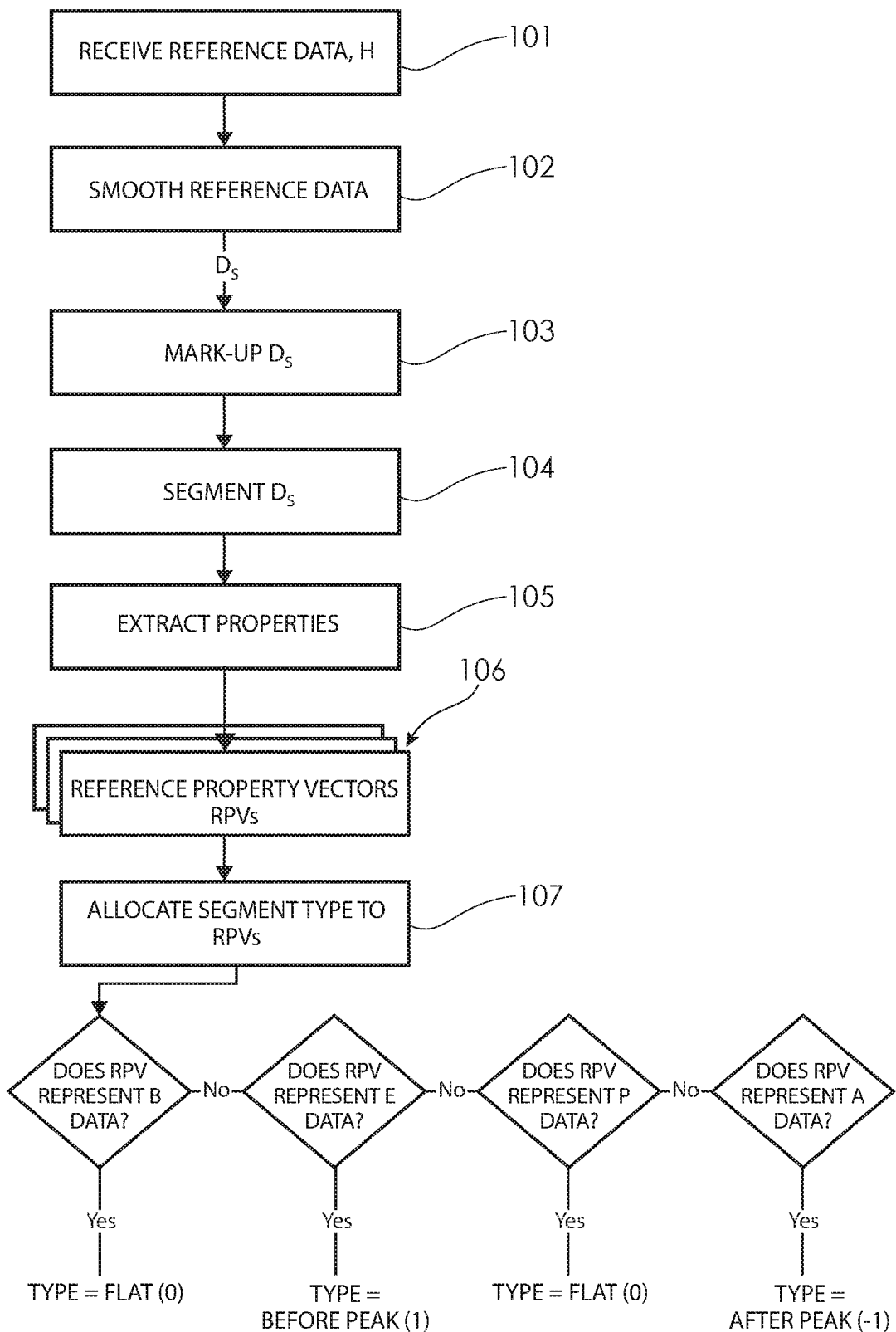
FIG. 1 is a flowchart showing steps in a method of generating a set of Reference Property Vectors each having an associated segment type, for use in an embodiment disclosed herein.

Referring firstly to FIG. 1, there is shown a method of generating a set of Reference Property Vectors for use with the present invention. In a step 101, reference data is received by a processing means which processes the reference data in such a way that a set of Reference Property Vectors 106 is obtained. Typically, the reference data is historical data obtained from one or more wetness sensors that have been used to sense urinary and/or faecal wetness events occurring in an absorbent article such as a pad. However, the sensors may alternatively/additionally sense other parameters such as temperature, pH, odour, gas, bio-analytes, pressure, movement, sound and the like. Alternatively/additionally, one or more of these other parameters may be utilised in the present invention e.g. by populating an element of one or more of the Reference Property Vectors used in the data analysis.

Ideally, the reference data is obtained for one or more pads and for a complete pad cycle. A pad cycle corresponds to a sequence of individual wetness events that occur during the wearing of a pad. As would be understood by the skilled addressee, a single wetness event does not necessarily cause the pad to reach its wetness absorbing capacity. Accordingly, sensor data for a complete "pad cycle" contains data corresponding to a number of individual wetness events in a sequence of events before the pad is changed (i.e. removed from the wearer and replaced with a fresh pad). Individual events in a pad cycle may be identified or referred to using an event sequence identifier. The event sequence identifier may be determined based on the number of events that have already been directed in a pad cycle.

In a preferred embodiment, reference data includes data obtained from more than one pad cycle observed for a particular subject. In a more preferred embodiment, the reference data includes data obtained from more than one pad cycle for a plurality of different subjects. The subjects may be indexed and/or grouped according to e.g. demographic indicators such as age, gender, health status, and the like. These demographic indicators may alternatively/additionally be used to populate an element in the Reference Property Vectors generated using the reference data, which vectors as discussed below.

Figure 4:
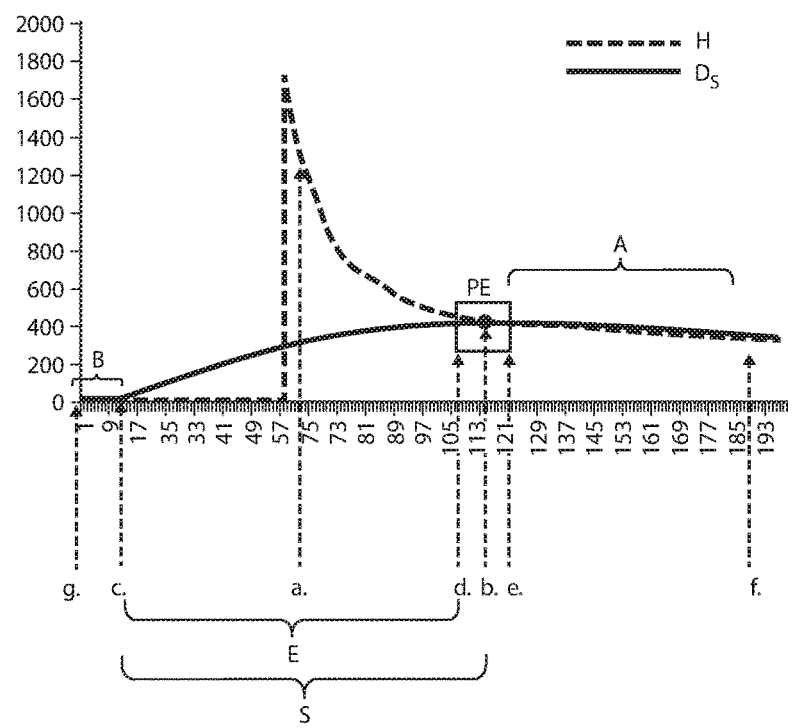
FIG. 4 is a schematic illustration representing reference data and smoothed reference data used to generate a set of Reference Property Vectors, according to an embodiment of the present invention.

FIG. 4 is a schematic illustration representing historical or reference data H corresponding to a wetness event. In a preferred embodiment, the local maxima in the unsmoothed reference data H representing the actual events are identified. Identifying the events in the unsmoothed reference data may be done using a manual marking up process by sight, or using an automated method. In some embodiments manual marking up is preferred because human oversight of the marking up process typically results in greater accuracy, particularly when the unsmoothed reference data contains artefact and spurious signal spikes that can intellectually be ruled out from comprising an "event peak", whereas an automated threshold detection approach may not be sufficiently sophisticated to make such distinctions.

In a preferred embodiment, the reference data H is smoothed in a step 102. Smoothing may be desirable to remove signal artefact and instabilities in the sensor signal. FIG. 4 also shows smoothed reference data $D_S$ derived from H. The smoothed data may be obtained using any suitable smoothing algorithm or formula. The smoothing algorithm typically uses a "smoothing window" which designates a section over which data is averaged in order to smooth the data values. Thus, the smoothing window may have a size S being the period over which data is averaged in order to achieve smoothed data output. The smoothing window size may be set statically or dynamically, and adjusted according to e.g. the sensor type used to obtain the reference data and/or the nature of the data and how much artefact or noise it contains. In one embodiment, the smoothing window size may be determined by trial and error.

As a result of smoothing the reference data, the location of various stages of wetness events represented in the data become shifted in time relative to the location marked up in the original (unsmoothed) reference data H. Accordingly, it is desirable in a step 103 to mark up the smoothed data. This involves identifying, in the smoothed reference data, data intervals that correspond with various stages of a wetness event in the unsmoothed reference data.

Typically, marking up the smoothed reference data, $D_S$, involves identifying the maximum value (corresponding to the event peak) and then working from there to identify the other event stages. Rising data values looking backward from the peak correspond to "Before Peak" event stage data. Decaying data values occurring after the peak can be identified as "After Peak" event stage data. The duration of this stage may be limited by a maximum decay period. Data occurring before the initial "Before Peak" event stage and occurring after an "After Peak" event stage but before a subsequent "Before Peak" event stage can be marked up as "Flat" event stage data. As the name suggests, "Flat" event stage data corresponds to event stages where there is little or no event activity of interest.

Thus, in an embodiment, the smoothed reference data Ds is marked up so that the segments comprised in the smoothed reference data are associated with particular segment types, based on event stages as follows:

segments comprised in a "Flat" event stage are identified as "flat" segment types;
segments comprised in a "Before Peak" event stage are identified as "Before Peak" segment types;
segments comprised in a "Peak" event stage are identified as "flat" segment types; and
segments comprised in an "After Peak" event stage are identified as "After Peak" segment types.

FIG. 4 has been marked up to identify these event stages. A "Flat" event stage is represented by smoothed data in section B. This corresponds to a sequence of smoothed data values which occur prior to the onset start of an event. The "Flat" event stage can be identified by looking for a flat section of smoothed data. An "After Peak" event stage is represented by smoothed data in section A and represents smoothed data values occurring after smoothed data values representing the "Peak" event stage. The decaying values from e. to f. represent "After Peak" event stage data A. This interval is limited by the length of a "Maximum Decay Period" (MDP) which may be set by trial and error, or as a function of previously processed data. The "Peak" event stage in the smoothed data is designated by the values inside the interval identified as PE which is bounded in time by points d. and e. Point d. represents the end of a sequence of "Before Peak" event stage data Point e. represents the start of a period of "After Peak" event stage data. The interval from c. to d. represents "Before Peak" event stage data E.

Ideally, the step of marking up the smoothed reference data involves establishing a selection of key parameters from the data. In addition to identifying the points and intervals above, these may include but are not limited to:

Smoothing window size S being the period over which data is averaged in order to achieved smoothed data output;
Local maxima in the unsmoothed reference data represented at a.;
A function N for transposing points in the unsmoothed reference data to smoothed reference data, where N is, in a preferred embodiment, configured according to the nature of the data and how much artefact or noise it contains. In one embodiment, the value determined by N is equivalent to the smoothing window size S and may be determined by trial and error. In another embodiment N is determined as a function of smoothing window size S. Corresponding maximum of the smoothed reference data represented at $$b \left(\text{where } b = a + \frac{N}{2}\right)$$

Slope orientation change point from "flat" to "Before Peak" event stage represented at $$c \left(\text{where } c = a - \frac{N}{2}\right);$$

Beginning point g. is the start of the "Flat" event stage represented by B (where g=c−B) and;
End point f. is the start if the "After Peak" event stage represented by A (where f=b+Af.=e.+A)

In a more generalized approach, a segment in an event stage may be represented by a vector having elements representing a degree of belonging or a probability to each of a plurality of different event stage types. In this approach instead of discrete transitions between stages being identified in the reference data, gradual changes may be designated. For example, event stage types may change gradually from Flat to Before Peak and from Before Peak to Flat from point a. to b., and c. to a. A linear, polynomial, sigmoid transition can be used for type transition between points a. to b.

In certain scenarios, special rules may be used for marking up the smoothed data. For example, two events may be combined if point c. in a current event happens before point e. of a previous event. Also, an event has no "Flat" event stage B if point c. in the current event occurs before point f. of the previous event. Where the time period between point f. of the previous event and point c. of the current event is less than B, then the "Flat" event stage commences only at point f. Additionally if there are segments of the data for which the identified events are nonsensical, then these areas are preferably marked as "unknown" so as to avoid contaminating the reference data.

Once the smoothed reference data has been marked up with event stages, it is processed in a step 104 to identify segments within the smoothed data which can then be labelled according to a "segment type". In one embodiment, the function used to process the smoothed data in this way may be referred to as a "Property Extractor Function" 105. Ideally, the outputs of the Property Extractor Function include a set of Reference Property Vectors 106 which are indexed or labelled according to their "segment type" (as determined by the Property Extractor Function). Thus, the "Property Extractor Function" may be applied to the smoothed data in finite segments, and the segments labelled according to when each segment occurs relative to the various event stages, based on the marked up smoothed data.

For example, the smoothed data may be represented at time $t^i$ by $S(t^i)$. The duration of the segment may be set to n units of time. According to an embodiment of the invention, a "Property Extractor Function" having notation f( ) may be represented as:

$$<p_1,p_2,\ldots,p_m>=f(S(t^i),S(t^{i+1}),\ldots,S(t^{i+n}))$$

$$R^n \to R^m \quad <P_1,P_2,\ldots,P_m>=f(S(t^i),S(t^{i+1}),\ldots,S(t^{i+n}))$$
$$R^n \to R^m$$

where $p_i$ corresponds to the extracted properties making up the extracted Reference Property Vector for the segment and m corresponds to the number of elements in the property vector.

The focus (or window) of the Property Extractor Function is then shifted by an offset of X units of time and the Property Extractor Function is applied on the next segment of smoothed reference data. The offset X may be determined by any suitable method. This may involve trial and error to ascertain an appropriate trade-off between precision and usefulness of the extracted property vectors, and computational power required to obtain those vectors. In one embodiment, the offset X corresponds to half the segment or window width. In an embodiment X is variable and it is derived using a function applied to previously determined segment types (or segment type vectors). For example, if a consecutive sequence of segment types are identical for a long duration, it may be desirable to extend the length of X. An algorithm may, through learning, adapt a value for X which is suitably based on previously processed data. Alternatively, X may be a static value.

Dynamic determination of the value of X may be desirable e.g. if the properties extracted from the moving window do not change much in a few consequent segments. This suggests that the sensor data is stable. In such cases, the offset X may be increased thereby reducing the number of segments to be processed and so reducing the processing time or computational burden, thus increasing the performance of the system when performing segment typing or classification. Conversely if the changes between the properties extracted from the moving window are significant from segment to segment, then the offset X may be decreased (or set to an initial or minimum value) to capture to a greater degree the changes represented in the data.

Determining a value for X dynamically may also be useful for generating a balanced set of Reference Property Vectors. For example, it may be useful to compute the length of the Before Peak, peak, After Peak and unknown stages from the marked up and smoothed reference data and then set a smaller X for the stages with shorter duration while setting a larger X value for the stages with larger length. In case of having dynamic X, the value of X is also recorded as one of the properties in each of segments.

Dynamic configuration of X could increase the performance of the segment classification step 206 when bottom and/or top edges of the moving window are crossed many times by the sensor data. This could indicate that the data is noisy in that area and in this case, X may be set to a larger value to avoid wasting computational effort on noisy segments of data.

Properties extracted and used to populate the property vectors (both Reference Property Vectors and Unknown Property Vectors discussed below) may include intrinsic properties and extrinsic properties. Intrinsic properties are properties which relate directly to the data contained within the window having focus. Extrinsic properties are not directly related to data within the window but may provide contextual information.

The properties for the Reference Property Vector may be extracted for a segment using any suitable means. Some of the properties may be identified manually. Alternatively/additionally, properties may be identified automatically by a processing means.

Example—"Property Extractor Function" Using Moving Window

The following section describes one example of an approach to extracting properties from data which employs a "moving window" approach to process reference data in finite segments. A moving window may be defined as a bounded window applied to data from which various 'properties' are extracted. The window may have any closed regular or irregular polygonal shape such as square, triangular, hexagonal, quadrilateral or the like, or it may be e.g. round, oval or elliptical. The window sides may each have the same or different pre-defined dimensions. Alternatively, one or more of the window sides may have a dimension, e.g. a length which varies, e.g. depending on the type or property/properties of previous segment types in a sequence. In one embodiment, the window has only one dimension e.g. it represents a line having width w or height h or a line which is curved or diagonal but which does not form a closed boundary. A window side length may alternatively be defined by trial and error.

In a preferred embodiment, the moving window is a rectangle having a pre-defined height h and width w. Ideally, height h is proportional to a voltage range embodied in the sensor data while the width w is proportional to a period of time. The inventors have found that a value for w which produces useful results is 20 seconds although window widths as short as 0.1 seconds or 0.5 seconds or 1 second or 10 seconds or e.g. 15 seconds may be useful. Similarly, window widths of longer than 20 seconds, e.g. 30 seconds, 40 seconds, 50 seconds, 60 seconds, 120 seconds, 180 seconds or even longer may be useful. A typical h value is in the order of e.g. 0.5% to 15% of maximum signal voltage, or bounded by about 10% of maximum signal voltage or even say 1%, 3% or 5% of maximum signal voltage may define h. Width w typically corresponds to the segment duration n referred to above.

Alternatively w and/or h may be determined dynamically to reduce the processing time for segment classification and/or to create a balanced set of Reference Property Vectors (see discussion of $X_P$ above). For example, if the top and bottom edges of the moving window are not crossed by sensor data then it could be deduced that the moving window is currently focussed on a flat section of data so the window width w may be increased. Width w of the window may be decreased when the sensor data intersects with the top and bottom edges of the moving window.

In another case, if there are many data intersections on the top and/or bottom edges of the moving window (which may imply that the data is noisy in that segment) then the height h and the width w of the moving window could be increased to capture the trend of data set appropriately which may increase the performance of the segment classification step 206. If h and w are set dynamically, then both values of h and w may be recorded as properties of each segment.

Each Moving Window is defined by a reference point $R^i(T,V)R^i(TI,V)$ in the smoothed data such that the moving window comprises any sensor data$R(T,V)$ $R^i(TI,V)$ where TI and VT, and V are $$t^i - \frac{w}{z} < T < t^i + \frac{w}{\left(\frac{z}{z-1}\right)}$$

and $$v^i - \frac{h}{z} < V < v^i + \frac{h}{\left(\frac{z}{z-1}\right)},$$

$z \in (0, +\infty]$.

where t is time;
w is window width;
z defines where the window's centre is located;
$v^i$ is voltage value of the signal at time i
$t^i$ is the time at i The moving window is ideally centred on a reference point $R^i$ (z=2) although this reference point need not be the "centre" of the window. Once properties are extracted for the segment of data within the window, the moving window is shifted by an offset of X. The size of the offset X influences the quantisation of the segments for which the properties are extracted. This in turn affects processing speed and efficiency. For instance, if X is half w, then there may be slower processing since adjacent windows overlap by 50% but there may be greater accuracy in the analysis which follows. There is a trade-off between speed and quality of the vectors obtained by shifting the window along in increments which are too large. Ideally, the offset X is no longer than w, although ideally there is some overlap between adjacent windows or "segments" for which properties are extracted.

Figure 5:
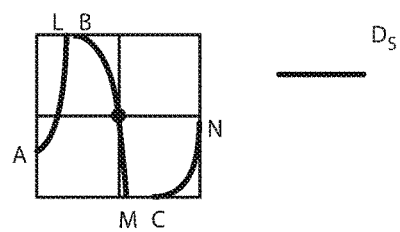
FIG. 5 represents a moving window applied to a segment of smoothed data according to an embodiment of the present invention.

FIG. 5 represents a moving window applied to a segment of smoothed reference data $D_S$. The number of intersections with the window boundaries in FIG. 5 indicate that the $D_S$ is a relatively noisy signal. In one embodiment, intrinsic properties (extracted using the Property Extractor Function) include e.g. the number of data samples in an edge of a moving window; the entry point on signal entry sides of the window and the exit point on signal exiting sides of the window. Entry and exit points may be quantified or described by reference to e.g. x and y coordinates of the sensor data, having respect to axes that can be applied to the window. Another way to quantify the entry and exit points is to calculate the distance between them (e.g. the distance between A and N in FIG. 5). Alternatively, entry and exit points may be quantified e.g. by a function calculating a distance between one or more reference points in the window (or on its boundaries) and the entry point and exit point.

Extrinsic properties typically include information which relates the data within the window to other segments in the data stream, which stream normally represents a number of events occurring over a period of minutes, hours, days or even longer. For example, extrinsic properties (extracted using the Property Extractor Function) may include a sequence identifier for the window, which gives context to whether a segment represents event data for a first event in a sequence of events in a pad cycle, or say a second or third event in the cycle. Alternatively/additionally extrinsic properties may include e.g. a previous maximum value of data encountered by the moving window; a duration representing the time elapsed since the start of the data stream (e.g. the start point, in time, of the window for that segment relative to the start point of the data set); time elapsed since a previous event peak in the data stream, or the like.

The properties may be extracted for a segment (identified by the moving window) using any suitable means. Some of the properties for the Reference Property Vector may be identified manually. Alternatively/additionally, properties may be identified automatically using processing means configured to apply one or more functions that extract the properties as the moving window passes over or propagates across the stream of data.

It is also contemplated that properties ascribed to a segment inspected using a moving window may include e.g. demographic information such as e.g. subject age, gender, weight, mobility, cognitive function etc, observational data pertaining to the period over which the sensor data is obtained (e.g. meal and fluid intake, toileting events etc) and other information such as movement, temperature, pressure and the like. These may include extrinsic and intrinsic properties.

FIG. 5 represents a moving window applied to a segment of smoothed data Ds and from which the following properties have been obtained:

Intrinsic Properties
    Window size w=10 sec; h=0.1 v
    Number entry points on left side 1
    Number entry/exit points on top side 2
    Number entry/exit points on bottom side 2
    Number entry points on right side 1
    Point A (entry): −0.2
    Point B (entry): 0.8
    Point C (entry): −1.3
    Point L (exit): 1.3
    Point M (exit): −0.95
    Point N (exit): −0.1
    Segment type: 1 (Before Peak)
Extrinsic Properties
    Event Number: 2
    Previous max value: 200
    Time since last event: 650
    Moving Speed: 1

Figure 6A:
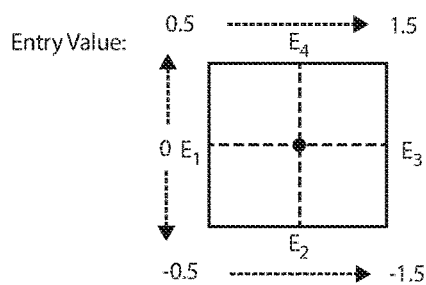
FIGS. 6a and 6b represent schema for attributing values to window entrance and/or exit properties according to an embodiment of the present invention.
Figure 6B:
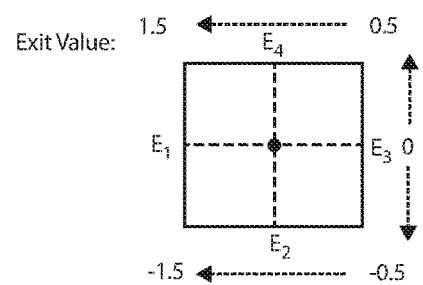

The entry and exit values may be quantified or identified in any suitable manner. In this example, they have been quantified using the schema identified in FIGS. 6a and 6b. FIGS. 6a and 6b represent schema for attributing values to window entry and/or exit properties.

One of the intrinsic properties identified above is "segment type" which is designated as "1" or "Before Peak". This is determined in a step 107 and in one embodiment, involves automatic and/or manual inspection of the smoothed reference data in which the segment is located, using the parameters discussed in relation to FIG. 4. Alternatively/additionally, manual inspection may be used to calibrate the result from an automatic inspection process or to identify noise in the smoothed data. In an embodiment, there are 3 segment types identified as follows:

| Segment type | Segment type ID |
|---|---|
| Flat ("B" data) | 0 |
| Before Peak ("E" data) | 1 |
| After Peak ("A" data) | −1 |

Optionally, there may be a fourth segment type known as:

| Segment type | Segment type ID |
|---|---|
| Unknown | 0 (null) |

Segments having type "unknown" are typically those segments in which the smoothed data corresponds noise or artefact, and for which a null or zero value is ascribed to minimise the adverse effect of those segments on the data analysis.

Each of the intrinsic and extrinsic properties forms an element of a Reference Property Vector extracted for the segment over which the window is positioned. The segment type may occupy an element of the Reference Property Vector, or may be associated with the Reference Property Vector in some other way. After the moving window has propagated across the reference data, and the properties extracted, a set of Reference Property Vectors 106 can be obtained. It is to be understood that the moving window need not propagate across the sensor data in chronological sequence. Alternatively, windows or segments may be extracted out of sequence or at random, and the Reference Property Vectors populated or determined out of sequence also.

Once the set of Reference Property Vectors 106 has been established from the reference data, it can be used in a process of analysing incoming data from sensors. Ideally those sensors are wetness sensors, for detecting wetness events in pads worn by incontinent subjects. The Reference Property Vectors may be obtained once and then used and re-used as necessary to analyse wetness sensor data to identify wetness events. There may be different sets of Reference Property Vectors obtained for use in different analysis scenarios. For example, one set of Reference Property Vectors may be used to analyse wetness sensor data from incontinent adult subjects, whereas a different set of Reference Property Vectors may be used to analyse wetness sensor data from incontinent babies, or children. Similarly, different sets of Reference Property Vectors may be used to analyse sensor data from different sensor types.

The term "Reference Property Vectors" is used herein to designate a set of segment properties for reference data. It is not to be limited to data represented as "vectors" as such. That is, the term Reference Property Vectors is to be taken as a reference to the reference data and properties that may be extracted from that data in segments, or as a reference to e.g. a look up table or the like in which properties extracted from the data are represented.

Figure 2:
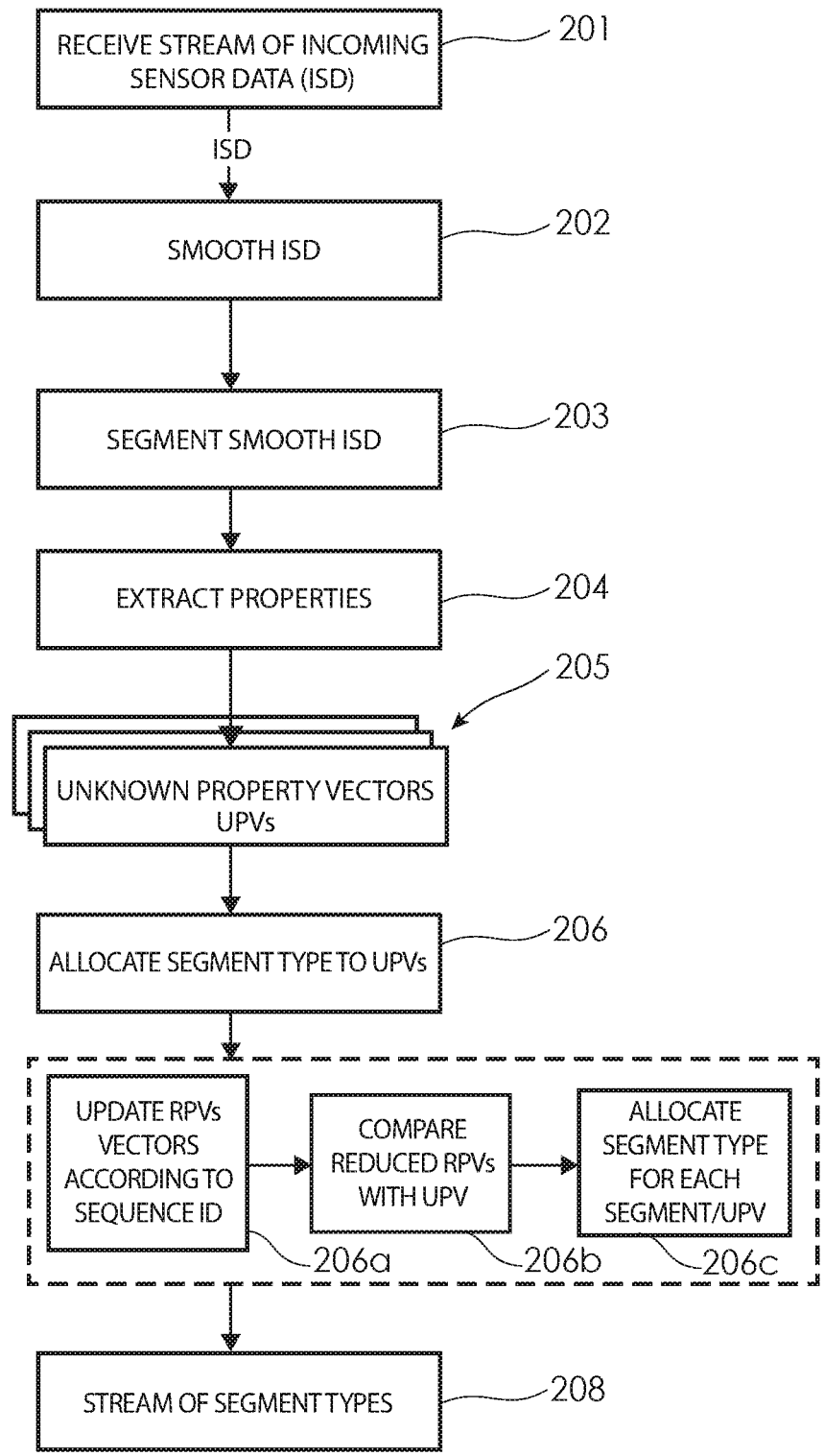
FIG. 2 is a flowchart showing steps in a method of determining segment type for a plurality of segments in a stream of incoming data, according to an embodiment disclosed herein

Referring now to FIG. 2, there is a flow chart showing steps in a method of determining segment type for a plurality of segments in a stream of incoming data from a sensor, according to an embodiment of the invention. In a step 201, a stream of incoming sensor data (ISD) from one or more sensors (e.g. wetness sensors) is received. Preferably, the incoming sensor data is smoothed in a step 202, using a smoothing algorithm or smoothing function. Smoothing of incoming data may be achieved in a manner similar to smoothing described in relation to the reference data discussed above.

In a step 203, the smoothed incoming data is segmented, and properties are extracted in a step 204. However in an embodiment the incoming data can be segmented and its properties can be extracted without being smoothed. Ideally, segmentation of the smoothed incoming data is done using a moving window method of the kind described above in connection with the Property Extractor Function utilised for segmenting and extracting properties for the smoothed reference data. The output of segmenting in step 203 and property extraction step 204 is conceptually referred to as a set of Unknown Property Vectors 205.

In a preferred embodiment, the same constraints of the moving window applied to the smoothed reference data may apply to the smoothed incoming data. Thus, the same moving window size may be used (having width w and height h) and the same window offset X may be used to segment the smoothed incoming data. Ideally, this is done substantially in real time although post-processing may be useful in certain circumstances. Once the smoothed incoming data has been segmented and the properties extracted, it becomes necessary to determine the "segment type" for each of the segments in the smoothed data set. Segmenting of incoming data and determining the properties of that data need not be done in a sequential (chronological) order in which the segments appear. The segments may be obtained and properties ascribed in a non-sequential or random order. However sequential processing may, in certain embodiments, give better computational efficiency. While the segment type may be manually determined for each of the segments in the smoothed reference data, that is laborious and not practically viable for processing large volumes of incoming data for use in real time analysis of wetness sensor signals obtained for a plurality of incontinent subjects.

Accordingly, an automated method step or group of steps 206 is used to determine the "type" for each of the segments in the smoothed incoming data and represented in the set of Unknown Property Vectors 205. Functions capable of determining segment type (a response variable) from the relationship or relevance between the Unknown Property Vector entries for a segment and the Reference Property Vectors (explanatory variables) may be employed. In embodiments, each of the one or more collections of vectors includes vectors from the set of Reference Property Vectors. Each of the one or more collections of vectors can be: a) derived from the set of Reference Property Vectors; or b) chosen from the set of Reference Property Vectors to form a subcollection of the set of Reference Property Vectors; or c) both a) and b).

As an example the selection of vectors to form the one or more collections may be performed in a random manner. In another example the vectors from the Reference Property Vectors are selected by reference to the Unknown Property Vector. In such embodiments, if the data needs to be processed as fast as possible the number of vectors in the one or more collections, compared to the number of vectors in the set of Reference Property Vectors, used in analysing the Unknown Property Vector is reduced to a smaller number. The number of Reference Property Vectors may be reduced randomly, e.g., a random subset of the Reference Property Vector is chosen. Processing of the incoming data can be achieved more quickly if the number of Reference Property Vectors is reduced which is particularly advantageous if the data needs to be processed as fast as possible. However, for some applications the number of vectors in the one or more collections may be more than the number of vectors in the set of Reference Property Vectors. For example to support fault-tolerance, e.g. in case one collection becomes unavailable, the rest of the collection can support analysing data with a same or similar performance as if all collections were available to use.

In another example, each of the one or more collections of vectors includes vectors randomly derived from the set of Reference Property Vectors. Accordingly, in such embodiments, each one of the collections include vectors each derived by combining two or more vectors from the Reference Property Vectors. In yet another embodiment, vectors in each of the collections may include vectors derived from the set of Reference Property Vectors or randomly selected from the set of Reference Property Vectors. The collection may contain repeated vectors. A subcollection of a collection is a portion of the collection so it may contain all, some or none of the vectors in the collection.

Figure 2A:
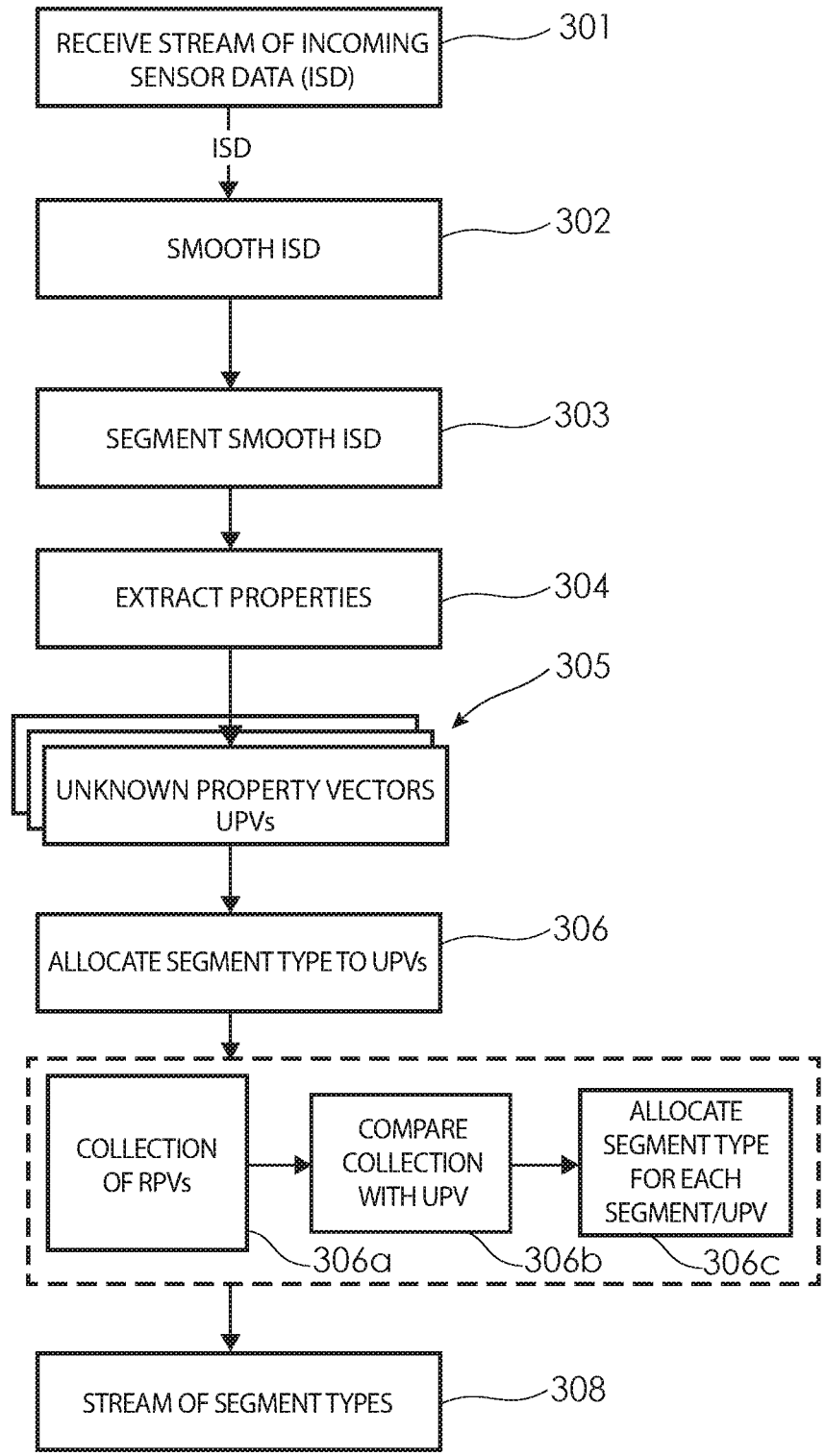
FIG. 2a is a flowchart showing steps in a method of determining segment type for a plurality of segments in a stream of incoming data, according to an embodiment of the invention.

Referring now to FIG. 2a, which illustrates a flow chart showing steps in a method of determining segment type for a plurality of segments in a stream of incoming data from a sensor, according to an embodiment of the invention. In a step 301, a stream of incoming sensor data (ISD) from one or more sensors (e.g. wetness sensors) is received. Preferably, the incoming sensor data is smoothed in a step 302, using a smoothing algorithm or smoothing function. Smoothing of incoming data may be achieved in a manner similar to smoothing described in relation to the reference data discussed above.

In a step 303, the smoothed incoming data is segmented, and properties are extracted in a step 304. However in an embodiment the incoming data can be segmented and its properties can be extracted without being smoothed. Ideally, segmentation of the smoothed incoming data is done using a moving window method of the kind described above in connection with the Property Extractor Function utilised for segmenting and extracting properties for the smoothed reference data. The output of segmenting in step 303 and property extraction step 304 is conceptually referred to as a set of Unknown Property Vectors 305.

In FIG. 2a, there is shown an approach to determining the relationship which maps segments represented by Unknown Property Vectors and segments represented by Reference Property Vectors including the step of selecting or obtaining collections of Reference Property Vectors involved in the analysis according to sequence at 306a. As described herein, the Reference Property Vectors may be included in the collection or collections randomly or with more sophisticated approaches which produces the collection of Reference Property Vectors 306a. In step 306b the Unknown Property Vector from 305 is compared with the collection of Reference Property Vectors (RPVs) and in a step 306c the relevant segment type represented in the collection of Reference Property Vectors is allocated to the Unknown Property Vector for the segment.

In embodiments, the sequence of segment types is determined, for each segment, by analysing the Unknown Property Vector by reference to one or more collections of vectors selected from a set of Reference Property Vectors. In further embodiments, the sequence of segment types is determined, for each segment, by comparing the Unknown Property Vector with a subcollection of vectors of each one or more collections of vectors concurrently. Additionally the Reference Property Vectors may be split into a plurality of collections and the processing is performed on each of the collections then the results are aggregated at the end to define the segment type. Accordingly, the sequence of segment types can be determined, for each segment, by aggregating the results of the comparison of the Unknown Property Vector with the collections of vectors or subcollections of vectors.

As mentioned above, the abovementioned methods and embodiments which involve the splitting of the Reference Property Vector or otherwise the selection of vectors from the broader library of Reference Property Vectors are particularly advantageous when dealing with large data sets in such a way that computational analysis can be performed in a parallel manner for obtaining results faster (i.e. in a "big data" framework). The term parallel (which can also be referred to as "parallel processing") is a type of computation in which calculations are carded out simultaneously. In the present context the term parallel refers to tasks in respect of which their processing can occur over time periods that are overlapping. In particular, a computational task, such as comparing the Unknown Property Vector with the one or more collections of vectors or any other processing task described herein as occurring in parallel, is broken down into several similar subtasks that can be processed independently and whose results are combined afterwards, upon completion. Note that the processing of two or more parallel tasks may or may not start at the same time and may or may not finish at the same time. It is to be appreciated, however, that selecting vectors from the library of Reference Property Vectors necessarily excludes some vectors from the analysis which may impact of the accuracy of the analysis and, hence, the accuracy of the method in detecting the occurrence of wetness events in an absorbent article. Thus, to improve the accuracy of analysis, whilst maintaining the technical benefits associated with improved computational analysis efficiency, more sophisticated approaches than randomly reducing the number of Reference Property Vectors included in the analysis are envisaged. For example, selecting a collection of candidates wherein each candidate represents a group of the Reference Property Vectors.

In embodiments, the vectors in the Reference Property Vectors are grouped together based on their similarity. Accordingly, the invention can include a process of selecting a collection of candidates wherein each candidate represents a group or cluster of the Reference Property Vectors. The group or cluster of the Reference Property Vectors may be grouped or selected based on their similarity. One way of grouping or selecting similar Reference Property Vectors is to perform a clustering analysis in which each of the Reference Property Vectors which have a similar property are grouped in a cluster. Each cluster can then be represented by one or more candidates (which may also be described as representative vectors). For example the centre of the cluster can represent the cluster or the centre of the more populated space in the cluster may be the candidate (representative vector) of the cluster. Similarly more than one candidate (representative vector) can represent a cluster. In any of the embodiments involving a candidate or representative vector, a set of Reference Property Vectors of lib-size vectors is reduced to cluster-num*candidate-per-cluster candidates in which cluster-num is the number of clusters and candidate-per-cluster is the number of candidates chosen to represent each cluster. The segment type of each candidate of each cluster is the representation of all the Reference Property Vectors segment types in that particular cluster. For example the segment type of a candidate of a cluster can be an average of all the segment types of the Reference Property Vectors in that cluster. In another example the segment type of a candidate of a cluster can be a weighted average in which the segment types of the Reference Property Vectors, in the cluster which are more similar (or are closer if a distance measurement is chosen) to the candidate, have more impact on the segment type of the candidate.

In some embodiments, the sequence of segment types is determined, for each segment, by selecting vectors from the set of Reference Property Vectors in respect of which at least one of the properties is relevant to the same property of the Unknown Property Vector and the Unknown Property Vector is analysed by reference to a set of the selected vectors that are relevant to the Unknown Property Vector. In some forms, during the processing of the incoming data in segments the Reference Property Vectors which are relevant (or more relevant) or similar (or more similar) to the Unknown Property Vector are included in the collection(s), set(s) or sub-set(s), or alternatively the Reference Property Vectors which are not relevant (or less relevant), not similar (less similar) or dissimilar (more dissimilar) to the Unknown Property Vector are removed. The relevant subcollection is identified based on the similarity of at least a property in an Unknown Property Vector to the same or an associated property in the Reference Property Vectors. For example if the $3^{rd}$ and the $5^{th}$ properties are used for determining similar vectors (or alternatively removing dissimilar vectors), then when an Unknown Property Vector is analysed, the Reference Property Vectors with similar values for the $3^{rd}$ and $5^{th}$ properties to the values for the $3^{rd}$ and $5^{th}$ properties of the Unknown Reference Property Vector are included in the collection(s), set(s) or sub-set(s), (or the dissimilar ones are removed).

The subcollection of vectors includes vectors in respect of which at least one of the properties are relevant, more relevant, similar or more similar to the same property of the Unknown Property Vector. In other embodiments, the subcollection of vectors excludes vectors in respect of which at least one of the properties are least relevant or are dissimilar to the same property of the Unknown Property Vector. In embodiments, to determine which are the similar Reference Property Vectors, a threshold may be used. The similarity is measured by any similarity measurement such as measuring the similarity of values of one or more properties in a vector to associated values of one of more properties of another vector, e.g., Euclidean distance of two vectors or Euclidean distance of a value of at least one property of two vectors. The properties that are used for removing vectors include the following non-limiting examples, namely: sequence ID, pad type, pad size, gender, or other properties. In another embodiment, a weight may be applied to each of the used properties, e.g. weighted distance.

In embodiments, the subcollection of vectors of the Reference Property Vectors includes vectors in respect of which at least one of the properties are similar to those of the Unknown Property Vector determined by a hierarchical procedure or a parallel procedure. Accordingly, some embodiments include a hierarchical procedure of including in the subcollection the Reference Property Vectors that comprise two or more of the properties that are relevant, more relevant, similar or more similar in a hierarchical order to the same two or more of the properties of the Unknown Property Vector. In the hierarchical procedure, at least one of the properties is used to remove the vectors that are not similar to the Unknown Property Vector and then the same procedure may apply with a different one or more properties of the remaining vectors.

In embodiments, the subcollection of the vectors includes the Reference Property Vectors that comprise two or more of the properties that are relevant, more relevant, similar or more similar in a hierarchical order to the same two or more of the properties of the Unknown Property Vector. The subcollection can include the Reference Property Vectors comprising the property that are the least distance apart from the same property of the Unknown Property Vector. The subcollection can include the Reference Property Vectors comprising the property that are a distance apart from the same property of the Unknown Property Vector that is less than a predetermined static or dynamic threshold.

A threshold which is used for removing the vectors that are not similar to the Unknown Property Vector or alternatively to keep the vectors which are similar to the Unknown Property Vector may be of a static or dynamic type. The static threshold does not change during the processing of incoming data. Alternatively the dynamic threshold can dynamically be set. The value of the dynamic threshold may change depending and/or base on one or more of the following reasons; how many wetness events are detected, detected segment types of the previous segments, geographical or environmental information (e.g. humidity level, temperature, barometric pressure) of where the incoming data is collecting from, the physiological information of the person that the incoming data is collecting from, the used property and the like.

In an embodiment, one or more of the collections are stored in one memory device which can be in one processing device or machine or can be on or distributed across separate memory storage devices on separate processing devices or machines or on the cloud. The processing of each collection can be performed on the same processing device or machine including the memory storage device in which the collection is stored, on separate processing devices or machines, on a single separate processing device or machine, or on the cloud. For example the collection can be stored on separate devices or machines and each collection is processed on the same device or machine that has the collection stored on it and then the results are aggregated on a separate device or machine.

In an embodiment, one approach to determining the relationship which maps segments represented by Unknown Property Vectors and segments represented by Reference Property Vectors is illustrated in FIG. 2 which shows, the step of updating the set of Reference Property Vectors involved in the analysis according to sequence ID at 206a. Reference Property Vectors having a different sequence identifier to the sequence identifier of the Unknown Property Vector are eliminated, which produces a reduced set of Reference Property Vectors. In another embodiment of step 206a, Reference Property Vectors are weighted according to their sequence identifier, and how relevant each sequence identifier is to the Unknown Property Vector. If the weighting is set to one for all vectors in the set of Reference Property Vectors (e.g. when the Sequence ID of the Reference Property Vector is the same as the Sequence ID of the Unknown Property Vector) then all the Reference Property Vectors are kept and so the reduced set of Reference Property Vectors is the same as the original set of Reference Property Vectors. In most cases however, the set of Reference Property Vectors will contain segments with different Sequence IDs. Those which have a closer relationship to the Sequence ID of the Unknown Property Vector may be given a higher weighting (or relevance ranking) than those having disparate Sequence IDs.

For example, for an Unknown Property Vector having Sequence ID=3, any Reference Property Vector also having Sequence ID=3 is allocated a weighting=1. Reference Property Vectors having a Sequence ID=2 or 4 may be allocated a weighting of 0.5 whereas Reference Property Vectors having e.g. Sequence ID=1 or 6 may be allocated a weighting of zero. Any Reference Property Vectors having a weighting of zero are excluded from consideration whereas the influence of the remaining vectors is modified in accordance with their weighting. This may be achieved using one or more functions.

In a step 206b the Unknown Property Vector from 205 is compared with the reduced set of Reference Property Vectors (RPVs) and in a step 206c the most common or relevant segment type represented in the reduced set of Reference Property Vectors is allocated to the Unknown Property Vector for the segment having the focus of the moving window. A more detailed outline of such a method is described in relation to the "Segment Classifier Function" exemplified below.

The segment type may be ascertained or classified using a deterministic or a non-deterministic approach in step 206. Using a deterministic approach, a segment may be attributed a single "segment type" based on e.g. the most commonly occurring segment type in the Reference Property Vectors having greatest similarity or relevance to the segment represented by the Unknown Property Vector. Yet in a more general approach, each segment type is represented by a segment type vector which represents the probability or likelihood of belonging of that segment to each of the segment types available. In one embodiment, a Segment Classifier Function a( ) used for non-deterministic determination or classification of segment type, may be represented mathematically as:

$$(T_1^n, \ldots, T_i^n, \ldots, T_k^n) = \\ a(p_1^n, \ldots, p_i^n, \ldots, p_m^n, T_1^{n-1}, \ldots, T_i^{n-1}, \ldots, T_k^{n-1}) \\ R^m \to R^k$$

or in another version as:

$$(T_1^n, \ldots, T_i^n, \ldots, T_k^n) = a(p_1^n, \ldots, p_i^n, \ldots, p_m^n,) \\ R^m \to R^k$$

where k is the number of different segment types available for attribution to a segment. $T_i^n$ is the likelihood that the segment n, which is represented by $(p_1^n, \ldots, p_i^n, \ldots, p_m^n)$, belongs to segment type i, and populates each element of a segment type vector $(T_1^n, \ldots, T_i^n, \ldots, T_k^1)$.

Example "Segment Classifier Function"

The following section describes two examples for determining segment type (segment type vector) for smoothed incoming sensor data by utilization of a K-NN algorithm and logistic regression, based on Reference Property Vectors extracted from smoothed reference data. This may be referred to as a "Segment Classifier Function" represented in FIG. 2 at step 206. However it is to be understood that any function capable of determining relationships may be suitable for classifying segments; the invention is not limited to a K-NN algorithm or logistic regression.

In one embodiment, each Unknown Property Vector has property elements corresponding to e.g. event sequence identifier; peak value of the previous event; time since last event; intrinsic window properties; and also an indicator of segment type. The indicator of segment type may be represented by a value (or a segment type vector of values) and is determined by the Segment Classifier Function. The event sequence identifier indicates the sequence order of the segment as it relates to a sequence of wetness events in a pad cycle. For instance, if the segment corresponds to a first wetness event in the pad cycle then the event sequence identifier is 1; if the segment corresponds to a second wetness event in the pad cycle then the event sequence identifier is 2, if the segment corresponds to a third wetness event in the pad cycle then the event sequence identifier is 3, and so on.

In an embodiment for determining the segment type, the Segment Classifier Function excludes from consideration those Reference Property Vectors having an event sequence identifier which is different to the event sequence identifier of the Unknown Property Vector. This may be used to produce a reduced set of Reference Property Vectors. In another embodiment the classifier function considers all the Reference Property Vectors. It is to be noted that although it may be conceptually helpful to have regard to a "reduced set" of Reference Property Vectors, physically producing such a reduced set (e.g. in memory of a computer or otherwise) may not be necessary. For example, if the event sequence identifier of the Unknown Property Vector is "2" then all of the Reference Property Vectors with an event sequence identifier other than "2" are merely disregarded in the processing steps, without physically producing a reduced set of Reference Property Vectors. Weighting may also be used. However having the relevant Reference Property Vectors separated in different tables increases the speed of segment type classification as the processing means does not need to compare the sequence identifier of the Unknown Property Vector with every single sequence identifier in the set of Reference Property Vectors.

Figures 7, 8:
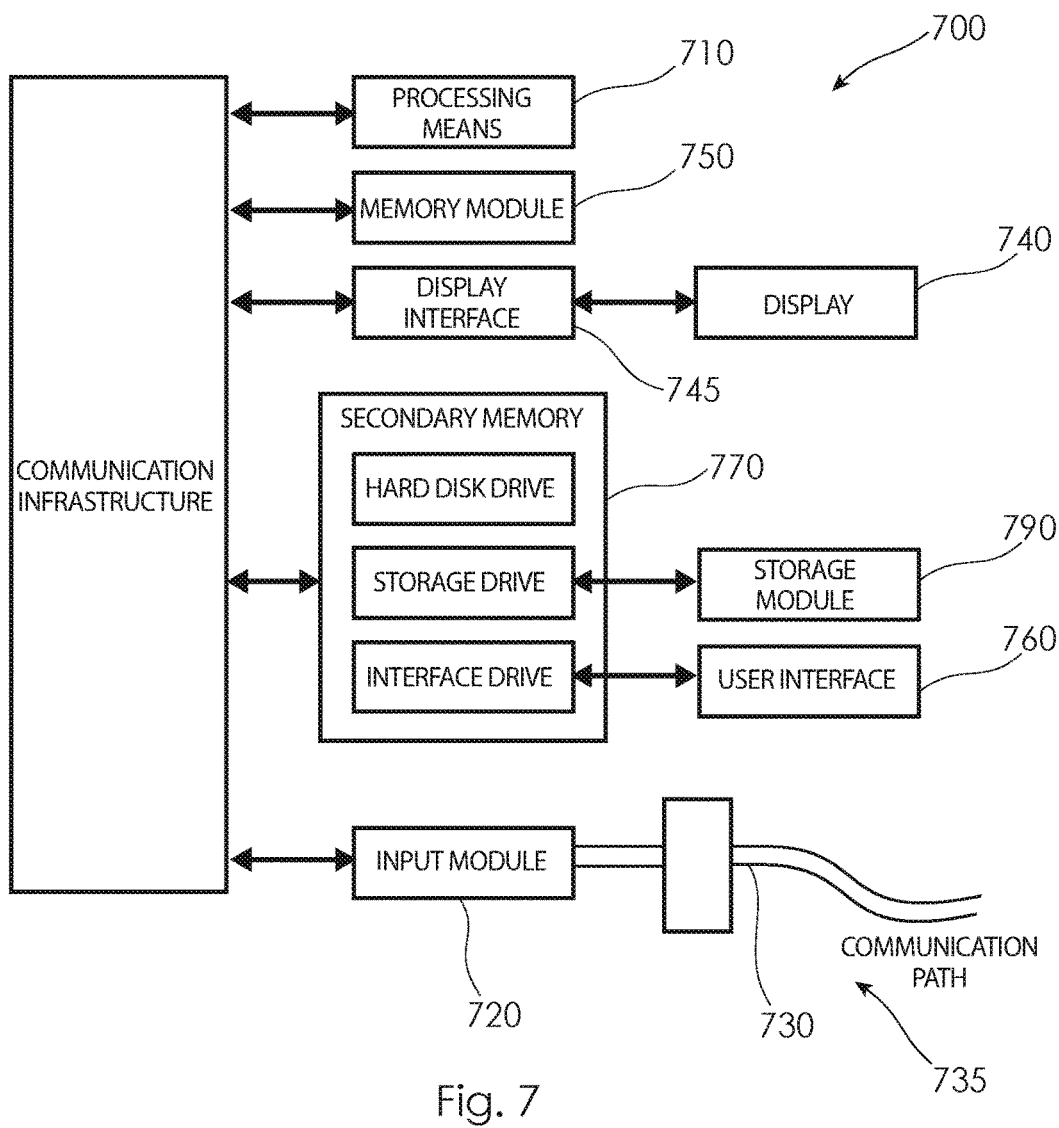

FIG. 8 represents a set of Reference Property Vectors. FIG. 9 represents a "reduced set" of Reference Property Vectors in which vectors corresponding to reference data segments having an event sequence identifier other than 2 have been removed. In each table, x is a mask which, for the sake of simplicity, has been used to replace actual values.

In some embodiments, FIG. 9 may be sufficient to identify type "1" (i.e. "Before Peak") as the segment type attributable to the Unknown Property Vector since it is the most commonly occurring in the reduced set of Reference Property Vectors presented in FIG. 9. However such an approach produces rudimentary results. In a preferred embodiment, with a K-NN algorithm the Segment Classifier Function compares the Unknown Property Vector to the reduced set of Reference Property Vectors. Ideally the comparison is a distance function e.g. Euclidean distance which measures the distance between the Unknown Property Vector, and each of the vectors in the reduced set of Reference Property Vectors.

Another embodiment uses a logistic regression algorithm to determine segment types for incoming data. The complete set or a reduced set of Reference Property Vectors may be used to derive the logistic regression algorithm in which the output represents the probability of a segment being one or more of After Peak, Before Peak, Flat or Unknown. The logistic regression algorithm may be generated using e.g. clustering or classification methods which group the reduced set or the complete set of the Reference Property Vectors into a number of classes or clusters, where each class or cluster can be represented by one or more chosen candidates. The segment type of the chosen candidate/s represents the frequency of each segment type occurring in that class/cluster which in turn, represents a probability of the class/cluster being of the type "After Peak", "Before Peak", "Flat" or "Unknown". One or more candidates representing a cluster or a class can be chosen to indicate the probability of the segment being of a particular type, the selection being based on one or more of: centre of the cluster or class, an average of the vectors in the cluster or class, a distance or similarity of each vector in the cluster or class to the representative candidate/s. The set of selected candidates and their probabilities may then used to derive the logistic regression function.

The logistic regression function can be applied to a set of Unknown Property Vectors to estimate the probability of a segment of incoming data being one or more of "After Peak", "Before Peak", "Unknown" or "Flat". In another embodiment a plurality of logistic regression models can be applied; where each model is chosen based on the similarity between the Unknown Property Vector and a class/cluster i.e. in an ensemble manner.

In an embodiment which utilizes a K-NN algorithm, the distance function may be computed by applying functions $u_i()$ on the distances between each of the properties in two vectors being compared, giving rise to dist( ) and yet another function h( ) is applied on the set of the functions $u_i()$ to compute a value representing the distance. Following is mathematical formulation for computing a distance for two vectors $\vec{x}=<x_1, x_2, \ldots, x_n>$ and $\vec{y}=<y_1, y_2, \ldots, y_n>$:

$$h(u_1(\text{dist}(\vec{x},\vec{y},1)), u_2(\text{dist}(\vec{x},\vec{y},2)), \ldots, u_n(\text{dist}(\vec{x},\vec{y},n)))$$

where dist( ) is a function to compute the distance between two vectors for a property, and $u_i()$ and h( ) are any types of functions that can determine relationships. In an embodiment the selection of dist and $u_i()$ and h( ) involves trial and error.

In one example, the calculated value is the distance between "peak value of the previous event" and "length from previous peak". FIG. 10 contains a reduced set of reference property values from FIG. 9 with Euclidian distances, as calculated for each of the vectors in the reduced set, appended in the right column. Ideally, the entries in the further reduced set of Reference Property Vectors from FIG. 10 are then sorted in order of increasing Euclidian distance, as represented in FIG. 11.

In one embodiment, according to the K-NN method, the vectors in the further reduced set of Reference Property Vectors corresponding to FIG. 11 are again further reduced by removing the vectors with a Euclidian distance greater than $\epsilon1$. In yet another embodiment, FIG. 11 is further reduced by removing the last n % vectors with largest distances. This results in elimination of some of the Reference Property Vectors which are not similar to the Unknown Property Vector and so to keep only the most "relevant Reference Property Vectors" as represented in FIG. 12. The most relevant Reference Property Vectors may be referred to as the k-nearest neighbours. In yet another embodiment none of the Reference Property Vectors are eliminated and so in this case the reduced set of Reference Property Vectors is the same as the original set of Reference Property Vectors with an extra field added representing the relevancy ratio of each Reference Property Vector to the Unknown Property Vector.

In an embodiment, a hierarchical elimination may be applied where a second Euclidean distance is calculated for a plurality of selected properties from the segment represented by the Unknown Property Vector and also for the corresponding properties in the k-nearest neighbours of the reduced set of Reference Property Vectors. Again, the entries are sorted according to the computed distance and referred to as "second k-nearest neighbours".

The last m % of the sorted distances in the second k-nearest neighbours set are eliminated from consideration. Typically, m is defined by trial and error. Alternatively, the last rows of a table representing the second k-nearest neighbours or the neighbours with distance m % greater than $\epsilon2$ are removed from the "second k-nearest neighbours" set to produce a set of "reduced second k-nearest neighbours". In an embodiment, the majority of the segment types in the "reduced second k-nearest neighbours" is then selected as the appropriate segment type to be ascribed to the Unknown Property Vector. In another embodiment, in addition to the type of vectors in the "reduced second k-nearest neighbours", the distance value of each vector is taken into account as the weight (importance) of the that vector's type.

The number of occurrences of each segment type in the reduced second k-nearest neighbours may be referred to as a number of votes. Where the number of votes for each segment type produces a result in which more than one segment type has a majority, then the type may be re-ascertained by changing the values of one or more of n or m or $\epsilon1$, or $\epsilon2$, or deciding on or influencing the type for the Unknown Property Vector vote based on the segment types determined for the previous segment; or applying a different distance function in step 206b. It is to be understood that the value of n or m or $\epsilon1$, or $\epsilon2$ may be determined using any suitable method. In an embodiment, their selection involves trial and error. The values of these variables may be static or dynamic.

In certain embodiments, it is desirable to avoid a situation where the probability or number of votes for all of the segment types is substantially similar. That is, it may be desirable to avoid a situation where there is no segment type (or sequence of segment types) which is more prevalent than the others, e.g. a scenario where all the segment types have a probability of 0.25. To adjust for this, the threshold value of one or more of n or m or $\epsilon1$, or $\epsilon2$ may be determined dynamically. Ideally the values are determined in such a way that the probability changes between adjacent segments in a sequence are gradual. An example demonstrating gradual variation in segment type probability is shown below:

|  | Segment number | | | | | | | | |
| --- | --- | --- | --- | --- | --- | --- | --- | --- | --- |
|  | i | i + 1 | i + 2 | i + 3 | i + 4 | i + 5 | i + 6 | i + 7 | i + 8 |
| Before Peak probability | 90% | 80% | 70% | 50% | 30% | 20% | 10% | 10% | 5% |
| After Peak probability | 10% | 20% | 30% | 50% | 70% | 80% | 90% | 90% | 95% |

The outcome of the segment type allocation for the complete set of smoothed incoming data is a stream of segment types 208 which are then used in an analysis process. In another embodiment, the outcome of the segment type allocation is a stream of segment-type vectors.

Correcting Imbalances in Reference Property Vector Segment Types

In one embodiment, the set of Reference Property Vectors used to determine the type of each segment in the smoothed incoming data may be unevenly balanced. This may occur e.g. as a result of smoothing or having many pad cycles in the reference data which contain no events. That is, the set of Reference Property Vectors contains many of one segment type but few of another type. In an embodiment, to avoid domination of the analysis by segment types which appear more frequently, the types which have fewer occurrences may be multiplied in the reference data set until the number of segment types are evenly balanced In another embodiment and for probabilistically determined segment-type vectors, votes utilised in the segment allocation step 206 may be weighted according to the number of occurrences of a particular segment type in the complete set of Reference Property Vectors. For example, if in the set of Reference Property Vectors the proportion of "Before Peak" segment types is double that of "Flat" segment types, then the likelihood that an incoming data segment is of type "Before Peak" should be halved in step 206. Other approaches may be adopted to account for unevenness in the segment type spread in the set of Reference Property Vectors.

Processing a Stream of Segment Types

Figure 3:
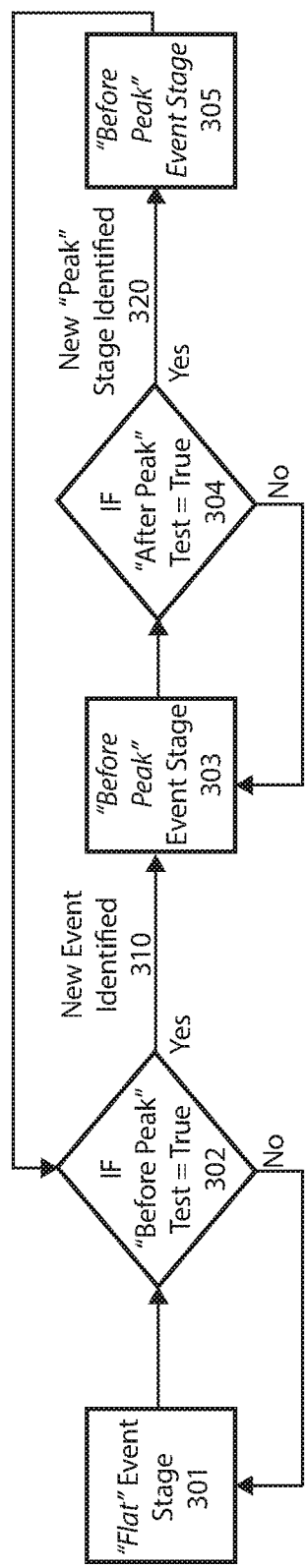
FIG. 3 is a state transition diagram for identifying wetness events in a stream of incoming data according to an embodiment of the present invention.

FIG. 3 is a state transition diagram representing steps in a method of processing a stream of segment types 208, to analyse the incoming data and then detecting an event. This processing occurs subsequent to the application of the segment classifier function to allocate segment types to a sequence of smoothed incoming data. An objective of the analysis is to detect events in the data and to this purpose, identify for a particular sequence of incoming data, the corresponding stage of an event, where stages are typically selected from the group including a "Flat" stage, a "Before Peak" stage, an optional "Peak" stage and an "After Peak" stage. Typically, it is assumed that incoming data prior to an event begins with a "Flat" stage at 301. At 302, a test is executed to determine if the sequence of segment types satisfies a "Before Peak" test. If the Before Peak Test is satisfied, then the event stage is deemed to be "Before Peak" at 303. The commencement of a "Before Peak" stage at 303 makes it possible to identify the start of a new wetness event in the pad cycle at 310. If the "Before Peak" test at 302 is not satisfied then the "Flat" event stage at 301 continues.

At 304, a test is executed to determine if the sequence of segment types satisfies an "After Peak" test. If the "After Peak" test is not satisfied, then the "Before Peak" event stage at 303 is deemed still to be current. If the "After Peak" Test is satisfied at 305, then it is possible to determine or infer the "peak" stage of the event in further processing, at 320.

Subsequent to that, if a "Before Peak" test is satisfied, then the event stage is deemed to be "Before Peak" at 303. Alternatively, the "After Peak" event stage at 305 is deemed to be still current.

The Before Peak Test and After Peak Test may each be implemented in any suitable manner. In one embodiment, where the segment type is determined for each Unknown Property Vector using a segment type value, the Before Peak Test and After Peak Test may implemented as outlined in Tests A and C (below). In another embodiment, where the segment type is determined for each Unknown Property Vector using segment type vector (comprising a plurality of segment type values), the Before Peak and After Peak Tests may be implemented as outlined in Test B.1, B.2 and C In another embodiment, outlined in Test C, $\alpha$, $\beta$, and i are set by applying functions k( ) l( ), and g( ) on a previous sequence of segment types or a previous sequence of segment type vectors. Determining the functions k( ), l( ) and g( ) may involve trial and error, or applying an optimization method to seek values or functions for k( ), l( ), and g( ) such that the performance of the event detection is maximized. In yet another embodiment k( ) and l( ) may derive a %, and $\beta$ %, as exemplified in Tests B.1 and B.2.

Test A

1. Set two thresholds, $\alpha$ and $\beta$, to be used in the Before Peak and After Peak tests respectively.
2. Set test size, l.
3. For each segment type in the stream of segment types 208, determine the sum of the previous l segments and store the value in T such that
    If $T \geq \alpha$,
       Before Peak Test=TRUE
    Else if $T \leq \beta$,
       After Peak Test=TRUE
4. An event peak stage is represented by the sequence of segment types following a "Before Peak" stage, and prior to the After Peak stage, where $\alpha > T > \beta$.

Application of Test A is Shown in Example A.

Example A

Showing Application of Before Peak and After Peak Test A

Assume a stream of segment types:
0,0,0,0,1,1,1,0,−1,null,1,1,1,1,1,1,null,0,−1,−1,−1,0,null, 1,1,−1,−1,−1,0,0
Where null can be attributed a segment type value=0.
Test size l=5
Before Peak threshold $\alpha=3$
After Peak threshold $\beta=-2$
The stream of values T is:

| $1^{st}$ | $2^{nd}$ | $3^{rd}$ | $4^{th}$ | $5^{th}$ | $6^{th}$ | $7^{th}$ | $8^{th}$ | $9^{th}$ | $10^{th}$ | $11^{th}$ | $12^{th}$ | $13^{th}$ | $14^{th}$ | $15^{th}$ | $16^{th}$ |
|---|---|---|---|---|---|---|---|---|---|---|---|---|---|---|---|
| 1 | 2 | <u>3</u> | 3 | 2 | 1 | 1 | 1 | 2 | 4 | 5 | 5 | 4 | 3 | <u>1</u> | <u>−1</u> |
| $17^{th}$ | $18^{th}$ | $19^{th}$ | $20^{th}$ | $21^{st}$ | $22^{nd}$ | $23^{rd}$ | $24^{th}$ | $25^{th}$ | $26^{th}$ | $27^{th}$ | $28^{th}$ | | | | |
| <u>−3</u> | −3 | −3 | −1 | 1 | 1 | 0 | −1 | −2 | −3 | −2 | −1 | | | | |

Test A reveals a positive Before Peak Test (signifying start of a new event) at the third value i.e. T=3 (underlined) and a positive After Peak Test (signifying end of peak stage and start of after event) at the $17^{th}$ value i.e. at T=−3 (underlined). An event peak is represented by the data corresponding to 3>T>−2. Accordingly the event peak is represented by data corresponding to the 15$^{th}$ and 16th values of T having values 1 and −1 respectively (shown with double underline).

Test B.1
1. Set two thresholds, α % and β %, to be used in the Before Peak and After Peak tests respectively.
2. For each Unknown Property Vector, identify the segment type in the segment-type vector having the highest likelihood of belonging.
3. For each segment type in the stream of segment-type vectors:
   if the segment type with highest likelihood of belonging is "Before Peak"
   and
   the likelihood is >α %,
      Before Peak Test=TRUE
         Define one event.
   if the event type with the maximum highest likelihood of belonging is "After Peak"
   and
   the likelihood is >β %,
      After Peak test=TRUE
4. An event peak stage is identified as the data values in the smoothed incoming data represented between the start of the "Before Peak" stage and the start of the "After Peak" stage.

Test B.2
A variation of Test B.1 that varies Step 3:
3. For each segment type in the stream of segment-type vectors:
   If the Before Peak type is >α %,
      Before Peak Test=TRUE
         Define one event.
   and
   If the After Peak type is >β %,
      After Peak test=TRUE An application of Test B.1 is shown in Example B.1.

Example B.1

Assume a stream of segment-type vectors where the segment types in each vector having the highest likelihood of belonging are as follows, where f represents flat, r represents Before Peak, n represents null and d represents After Peak segment types:
f 30%, r 50%, r 89%, n 90%, f 95%, r 30%, d 10%, d 30%, r 20%, d 70%, f 20%, d 50%
   Threshold α=80
   Threshold β=50

Test B.1 reveals a positive Before Peak Test (signifying start of a new event) in data represented by the 3rd segment (where r=89%) in the sequence of segments obtained from the incoming data. Similarly, Test B.1 reveals a positive After Peak Test (signifying end of peak stage and start of after event) at the 10th segment (where d=70%).

Test C
(a) Set two variable thresholds α and β, which are derived by applying functions k( ) and l( ) on the previous segment types (or segment type vectors), to be used in the Before Peak and After Peak tests respectively
(b) Set variable test size l by applying g( ) on previous segment types (or segment type vectors)
(c) For each segment type (or segment type vector) in the stream of segment types 208, apply z( ) on the previous l segments and store the value in T such that
   If T≥α,
      Before Peak Test=TRUE
   Else if T≤β,
      After Peak Test=TRUE (d) An event peak stage is represented by the sequence of segment types after Before Peak and prior to the After Peak values where α>T>β.

In Test C, the output of applying z( ) on the previous l segments-types (or segment-type vectors) is a single value or a vector stored in T. An example z( ) may be as follows:
T=0
if (AND(if segment$_i$ is After Peak, if segment$_{i-1}$ is After Peak, . . . , if segment$_{i-l}$ is After Peak)=True)
T=1
if (AND(if segment$_i$ is Before Peak, if segment$_{i-1}$ is Before Peak, . . . , if segment$_{i-l}$ is Before Peak)=False)
where i is the index of the current segment. Each of the operands in the AND( ) operation can be computed by any of Tests A, B.1, B.2 and C. In a variation of Test C, the output of z( ) can be a continuous value between 0 to 1.

Each of Tests A, B.1, B.2 and C are useful in determining where, in a sequence of incoming data values, an event such as a wetness event occurs. The tests are intended to be robust to signal artefact and to produce more reliable results than event detection methods which employ mere threshold detection. The approach adopted in the present invention employs algorithms that have regard to windows of data rather than single points, and which windows are evaluated according to a plurality of data properties which may be either intrinsic to that window, or extrinsic to the window, or both. This approach gives greater substance to the analysis output.

Optimizing Thresholds for after Peak and Before Peak Tests

In an embodiment, it is possible to optimize values for one or more variables employed in the "After Peak" and "Before Peak" tests. These variables include e.g. thresholds: l, α, β, A and B. Values for these variables may be optimised during an assessment or live analysis of incoming sensor data (live-optimization) or in an offline mode (offline optimization). In an offline optimization, the Segment Classifier Function generates the stream of segment types (or segment type vectors) and an optimisation procedure is applied. The optimization procedure determines the value of the variable (or threshold) according to one or more objectives such as (i) correctly identifying the maximum number of the events occurring in the data; (ii) minimising the number of false-positives; (iii) minimizing the number of false-negatives, and (iv) maximising the number of true-negatives. Typically this is an iterative procedure. In a live-optimization procedure the values of the variables are adjusted during the live analysis based on observational feedback data e.g. from a subject who is wearing a sensor pad or an observer who is monitoring the subject e.g. a carer. Thus in the case of wetness sensing for incontinence monitoring and analysis, when an actual voiding event occurs, the wetness event detection system records a time-stamp. The system then applies an optimization procedure to determine the optimized values of control variables or thresholds which give rise to maximising the number of the events being correctly identified, minimising the number of false-positives and false-negatives, and maximising the number of true-negatives.

Referring now to FIG. 7, there is shown a wetness event detection system 700 for detecting wetness events in sensor data obtained from one or more wetness sensors in a pad worn by a subject. The system 700 includes a communication infrastructure 780 for functional interoperability of the various system components. An input module 720 is configured to receive and optionally pre-process sensor signals from the one or more wetness sensors. Pre-processing may involve e.g. smoothing the data. A storage module 790 stores reference wetness data. The reference wetness data may be pre-processed into a set of Reference Property Vectors, and may be grouped according to e.g. sensor type, patient type (e.g. infant versus adult) or in any other manner considered to improve event analysis.

The system further includes processing means 710 configured to process sensor data obtained from the input module to identify wetness events in the sensor data. The input module may receive the sensor data through any means 730 such as wireless networks, wired networks, USB, flash drive, cloud memory or the like. Sensor data may be provided to the system via communications path 735.

A memory module 750 stores instructions that cause the processing means 710 to perform a method of analysing incoming data as described herein. A user interface 760 is configured to receive inputs from a user or operator. This enables a user or operator to interact with the system e.g. to cause the display means 740 which is communicatively coupled with the processing means via display interface 745 to display wetness event information, or change parameters used in the analysis, append data to reports and the like. It also facilitates input of observational feedback data for use e.g. in real-time (or offline) optimization of variables/thresholds used in the automated analysis. In an embodiment, the system 700 may also be used to generate Reference Property Vectors as described herein.

Although the present invention has been described and in parts, exemplified in the context of signal analysis for wetness sensor signals and particularly for use in incontinence monitoring, it is to be understood that the analysis and processing methodology described herein has application in a broad range of signal analysis problems where mere threshold detection methods are either unsuitable or inadequate.

Throughout this description and claims, the term "pad" is used. This term is to be interpreted as including diapers, liners, nappies, dressings and other absorbent articles and devices that absorb moisture such as urine, faces, blood, plasma and the like. These may be worn by or applied to adult subjects or babies, children or adolescents. Alternatively/additionally they may be worn by or applied to animal subjects.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

The invention claimed is:

1. A wetness event detection system for processing incoming data to detect urinary and/or fecal wetness events in incoming data obtained from one or more wetness sensors in an absorbent article worn by a subject, the system including:
   (a) an input module configured to receive and optionally pre-process sensor signals from the one or more wetness sensors;
   (b) a storage module configured to store reference wetness data;
   (c) a processor configured to process incoming data from the input module to identify urinary and/or fecal wetness events in the incoming data;
   (d) a memory module storing instructions that are executable by a processor to perform a method of analysing incoming data;
   (e) a user interface configured to receive inputs from a user; and
   (f) a display communicatively coupled with the processor and configured to display wetness event information derived from the processor,
   wherein the processor processes the incoming data to output a sequence of segment types by extracting one or more properties of an incoming data segment and forming an Unknown Property Vector for each segment of data in the incoming data; and processing the sequence of segment types to identify urinary and/or fecal wetness events in the incoming data; wherein the sequence of segment types is determined, for each segment, by analysing the Unknown Property Vector by reference to one or more collections of vectors from a set of Reference Property Vectors.

2. The system of claim 1, wherein each of the one or more collections of vectors are:
   a) derived by the processor from the set of Reference Property Vectors; or
   b) chosen by the processor from the set of Reference Property Vectors to form a subcollection of the set of Reference Property Vectors; or
   c) both a) and b).

3. The system of claim 1, wherein each of the one or more collections of vectors are determined by the processor by reference to the Unknown Property Vector.

4. The system of claim 1, wherein each of the one or more collections of vectors includes vectors randomly selected by the processor from the set of Reference Property Vectors.

5. The system of claim 1, wherein each of the one or more collections of vectors includes one or more vectors representative of groups or clusters of vectors from the set of Reference Property Vectors.

6. The system of claim 1, wherein the one or more collections of vectors are distributed across one or more storage modules.

7. The system of claim 1, wherein the properties of the incoming data segment are derived from an intersection of the incoming data with the one or more boundaries of a moving window.

* * * * *